United States Patent [19]

Meyers

[11] Patent Number: 4,955,885
[45] Date of Patent: Sep. 11, 1990

[54] SURGICAL SLIDER INSTRUMENT AND METHOD OF USING INSTRUMENT

[75] Inventor: John E. Meyers, Columbia City, Ind.

[73] Assignee: Zimmer, Inc., Warsaw, Ind.

[21] Appl. No.: 287,244

[22] Filed: Dec. 21, 1988

[51] Int. Cl.$^5$ .............................................. A61F 2/00
[52] U.S. Cl. ........................................ 606/53; 606/61
[58] Field of Search ............... 128/69, 92 R, 92 EA, 128/92 E, 92 EC, 92 V, 92 VZ, 303 R, 346; 606/53, 61

[56] References Cited

U.S. PATENT DOCUMENTS

| D. 291,729 | 9/1987 | Greig | D24/27 |
|---|---|---|---|
| 1,085,461 | 1/1914 | Michaelis | 81/419 |
| 4,347,845 | 9/1982 | Mayfield | 128/92 V |
| 4,382,438 | 5/1983 | Jacobs | 128/69 |
| 4,409,968 | 10/1983 | Drummond | 128/69 |
| 4,641,636 | 2/1987 | Cotrel | 128/69 |

OTHER PUBLICATIONS

Stuart, Inc. Publication–"Universal Instrumentation (CD) For Spinal Surgery"–Dr. Cotrel/Dr. Dubousset–1985.
Sofamor Company Publication–"Universal Instrumentation (CD)"–Dr. Cotrel/Dr. Dubousset–No date Available.
Zimmer, Inc. Publication–"Gaines Spinal Hook Distractor"–1986 (lit. No. 97-1260-05).
Zimmer, Inc. Publication–"Harrington Spinal System–Six–Ratchet Distraction Rods, Gaines Hook Distractor"–1987 (Lit. No. 97-2250-01).
Zimmer, Inc. Publication–"Bobechko Spinal Hook System, Surgical Technique"–1984 (Lit. No. 84-008-85-04-0300).
Zimmer, Inc. Publication–"Wisconsin Compression System"–1980 (Lit. No. B 2260).
Zimmer, Inc. Publication–"Edwards Spinal Fixation System"–1984 (Lit. No. 84-008-8504-0281).
Zimmer, Inc. Publication–"Scoliosis & Spinal Instrumentation Systems, Standard Line and Specialty Products"–(1980 Spinal Catalog)–(Lit. No. B-2255-4)-pp. 27, 29, 49, 56–59.
Zimmer, Inc. 1987 Catalog p. D20–Note the 99-5051 T-Pusher as well as other Spinal Instruments.

Primary Examiner—Robert A. Hafer
Assistant Examiner—Lynda M. Cofsky
Attorney, Agent, or Firm—Margaret L. Geringer

[57] ABSTRACT

A surgical instrument to aid in maneuvering a slideable member along a rod or other base member. The instrument has a distal tip which straddles the slideable member to provide for longitudinal movement of the slideable member in either longitudinal direction. The instrument also allows downward force to be applied to the slideable member. The instrument also may be used to assist in introducing the slideable member into an opening of another device.

10 Claims, 2 Drawing Sheets

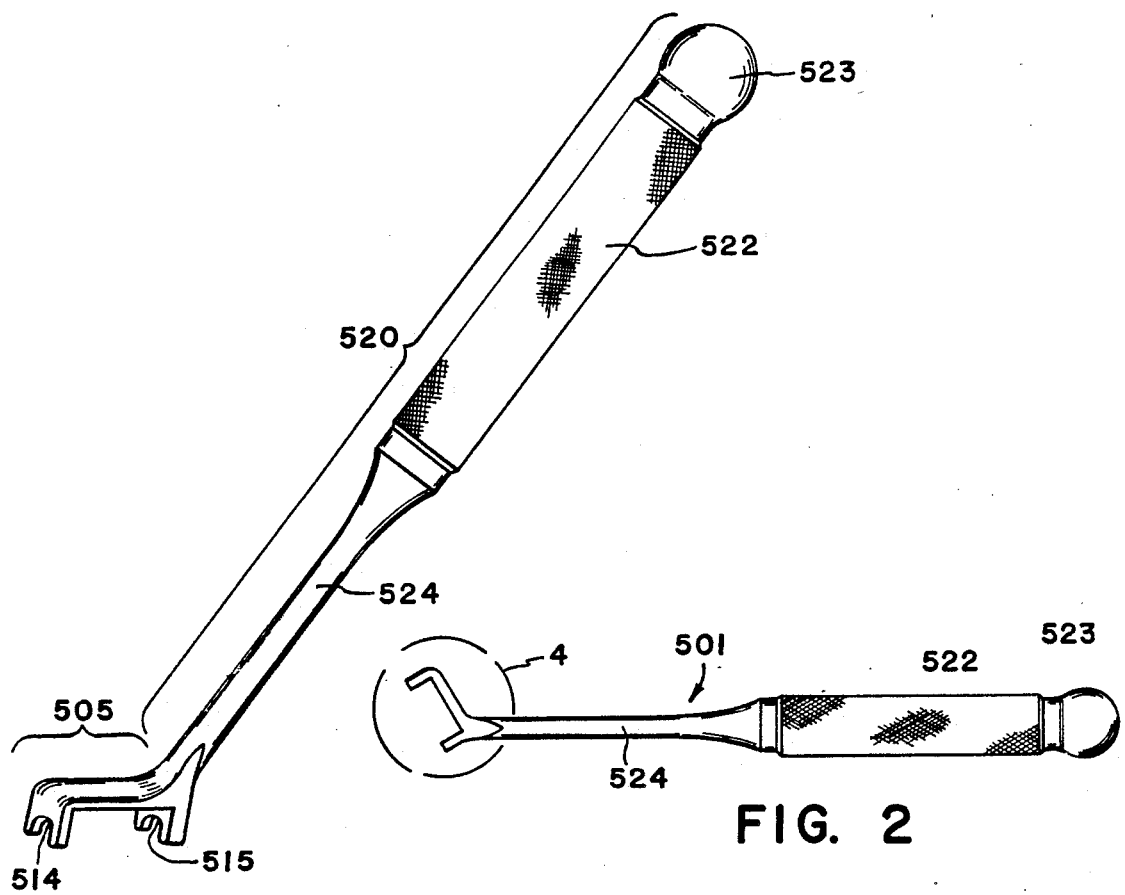
FIG. 1
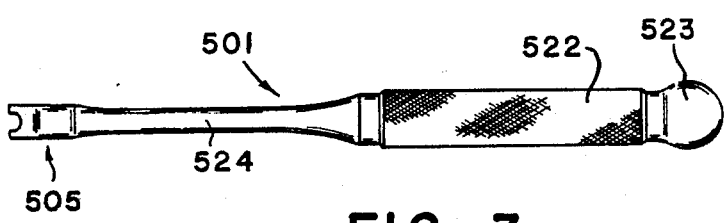
FIG. 2
FIG. 3
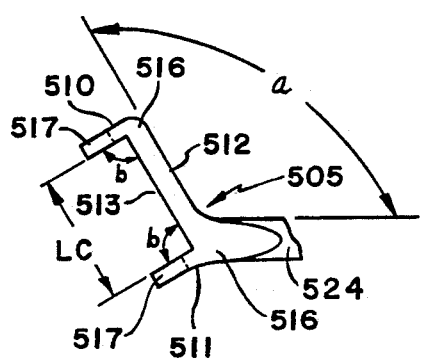
FIG. 4
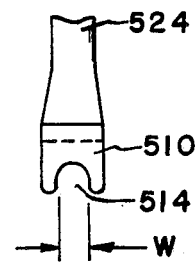
FIG. 5

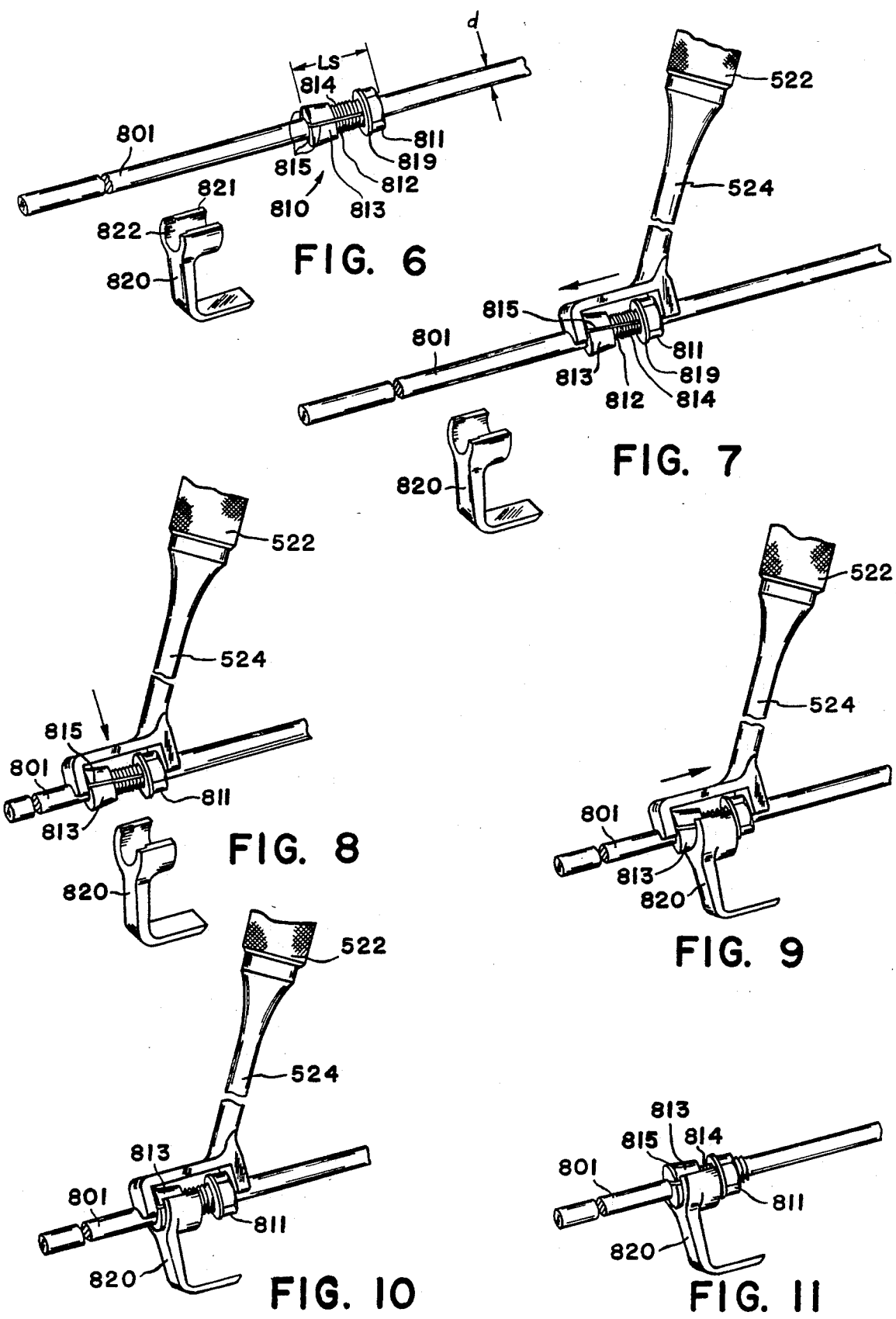

SURGICAL SLIDER INSTRUMENT AND METHOD OF USING INSTRUMENT

BACKGROUND OF THE INVENTION

The present invention relates to a surgical instrument which is used to aid in maneuvering a slideable member along an elongated rod or other base member. The instrument is particularly suitable for use with spinal implants and instrumentation, although it is not limited thereto.

Heretofore, various surgical spinal systems have utilized slideable sleeve-type members which are adapted to slide along an elongated rod or base member to a desired location. Typically, a surgeon will slide or maneuver the slideable members manually along the rod to the desired locations.

U.S. Pat. No. 4,461,636 to Cotrel describes a spinal system which includes slideable locking elements 30. A system which corresponds to this patent is marketed by the Sofamor Company or Stuart Company and is referred to as the CD or Cotrel/Dubousset System. This CD System includes instruments in conjunction with this spinal system which include a single rod receiving opening for fitting about the spinal rod or pin 20. These instruments, such as Sofamor/Stuart's Hook Pusher (84612) and Hook Driver (84613), can face up against a surface of a slideable element, such as 30, to push it in a given direction, and potentially into anchoring member 23.

OBJECTS OF THE INVENTION

A principal object of the invention is to provide a surgical instrument which straddles a slideable member and aids in sliding this member longitudinally along an elongated rod or base member in either longitudinal direction to maneuver the slideable member to the desired location.

A further object of the invention is to provide an instrument which aids in introducing the slideable member into an opening of another device.

A still further object of the invention is to provide an instrument which may be used to seat or more securely locate the slideable member once it has been introduced into the opening of another device by subsequently applying longitudinal force to the slideable member.

Another object of the invention is to provide an instrument which includes a cavity for accepting the slideable member, the cavity having a predetermined length which may be used as a gauge when utilizing the instrument with a slideable member having adjustable length features to gauge the desired starting length of the adjustable slideable member, if desirable.

A further object of the invention is to provide an instrument having a cavity for straddling a member which is slideable along an elongated rod, wherein the length of the cavity is substantially aligned with the length of the rod.

SUMMARY OF THE INVENTION

The present invention provides a surgical instrument for use with a slideable member which is located along an elongated rod. The instrument includes a distal tip with an elongated handle extending therefrom. The tip includes first and second extending members spaced apart from each other and connected by an interconnecting portion therebetween, thus providing a cavity between the first and second extending members. The cavity is open on at least one side and is adapted for accepting a portion of the slideable member therein for straddling the slideable member between the first and second extending members. The first and second extending members each include a recess in a side which corresponds to the open side of the cavity, each recess extending into the respective extending members. The first and second recesses align longitudinally with each other, providing an uninterrupted aligned passageway from the first recess connecting to the cavity which connects to the second recess, thus enabling this passageway to accept a portion of the elongated rod therein.

BRIEF DESCRIPTION OF THE DRAWINGS

These features and objects of the invention, as well as others, will become apparent to those skilled in the art by referring to the accompanying drawings:

FIG. 1 is a perspective view of the surgical instrument according to the present invention;

FIG. 2 is a side view of the instrument of FIG. 1;

FIG. 3 is a top view of the instrument of FIG. 1;

FIG. 4 is a partial enlarged view of the distal tip of the instrument circled at "4" in FIG. 2;

FIG. 5 is an enlarged front end view of the tip of FIG. 4;

FIG. 6 illustrates a perspective view of a slideable member positioned along an elongated rod which is located in spatial relation to an open-back member;

FIGS. 7-10 are perspective views illustrating the surgical instrument of FIGS. 1-5 being utilized to maneuver the slideable member of FIG. 6; and FIG. 11 is a perspective view illustrating the slideable member located in the desired position within the open-back member.

DETAILED DESCRIPTION OF THE INVENTION

FIGS. 1-5 illustrate a particularly advantageous embodiment of the surgical slider instrument 501 of the present invention. FIGS. 6-11 illustrate the use of this instrument 501 in conjunction with a slideable member 810 which is slideable along elongated rod 801 for eventually positioning slideable member 810 within the open-back member 820. It is noted that this instrument is particularly suitable for use as a spinal instrument, in particular for use with spinal implants which utilize a slideable sleeve member (such as 810) along a spinal rod (such as 801) for positioning within an open-back member 820 such as an open-back spinal hook (as shown in FIGS. 6-11), or any other suitable open-back spinal fixation devices (other types not shown). The particular slideable member 810 and open-back member 820 illustrated in FIGS. 6-11 are utilized in conjunction with the spinal implant system described in co-pending patent application Ser. No. 287,245, filed Dec. 21, 1988 to Cozad et al. which is incorporated herein by reference. However, it is noted that the features of this surgical slider instrument may be utilized with any suitable slideable member which slides along an elongated rod or base member, and is not limited to spinal applications.

The instrument 501 includes a distal tip 505 or working end portion and an elongated handle 520 extending therefrom. The handle, as shown, may suitably include a gripping portion 522 which blends into a narrower portion 524 which attaches to the distal tip 505. The handle 520 may also include an enlarged proximal portion 523.

The tip 505 includes first extending member 510 and second extending member 511 spaced apart from each other and connected by an interconnecting portion 512 therebetween, thus providing a cavity 513 between the first and second extending members 510 and 511. The cavity defines a fixed distance or length "LC" between the first and second extending members 510 and 511. This length of the cavity, between the first and second extending members, is substantially aligned with the length of the rod 801. The cavity is open on at least one side and thus is adapted for accepting a portion of the slideable member 810 therein for straddling the slideable member 810 between the first and second extending members 510 and 511. The instrument 501 straddles the length of the slideable member, but may only accept a portion of the width or height of the slideable member within the cavity 513. The inner surfaces of the extending members 510 and 511 which face inward toward the cavity 513 will be adjacent the respective ends the slideable member 810 as shown in FIGS. 7–10.

It is noted that the cavity 513 as shown in the FIGS. 1–5 is open on three sides although it could be designed to have an opening on only one side for accepting the slideable member 810 within the cavity 513. The first and second extending members each have a side 517 corresponding to the at least one open side of the cavity 513. Each corresponding side 517 includes a recess 514 and 515 extending into the respective extending members 510 and 511. The first recess 514 aligns longitudinally with the second recess 515 providing an uninterrupted aligned passageway from the first recess 514 connecting to the cavity 513 which connects to the second recess 515, thus enabling this passageway to accept a portion of the elongated rod therein. The elongated rod 801 passes through the slideable member 810 as shown in FIGS. 6–11. It is noted that the recesses 514 and 515 are located on sides 517 of members 510 and 511, which are oppositely located to sides 516 of members 510 and 511. Sides 516 connect the members 510 and 511 to the interconnecting portion 512. However, if desirable, the recesses could be located in either of the sides of members 510 and 511 adjacent sides 516 (this alternative not shown), since the corresponding sides of cavity 513 are open. This could allow side entry of the slideable member 810 into cavity 513 rather than bottom entry (the latter of which is shown), if desirable.

The recesses 514 and 515 may suitably have a shape which corresponds to the shape of the rod 801. In the embodiment shown, the rod 801 is cylindrical, and thus, the recesses 514 and 515 are substantially semi-cylindrical in shape to fit over the rod 801 as shown in FIGS. 7–10. The width "W" of the recesses 514 and 515 are suitably sized to allow the recesses to fit over the rod 801 having diameter "d."

The first and second extending members 510 and 511 are substantially planar, as is the interconnecting portion 512 therebetween. The members 510 and 511 are each substantially perpendicular to the interconnecting portion 512, thus forming angles "b" of about 90°. The handle 520 forms an angle "a" of about 120° with the interconnecting portion 512. The handle 520 connects to the distal tip 505 at a location more toward the second extending member 511 than the first extending member 510.

The first and second extending members 510 and 511 are spaced apart from each other at a predetermined distance. This distance or length "LC" may be suitably sized to straddle a slideable member 810 having a particular length "LS."

The slideable member 810, as shown in FIGS. 6–11, may be a slideable assembly rather than a single slideable member. The slideable member 810 of FIGS. 6–11 includes a locking sleeve 812 having a tapered portion 813 and a threaded portion 814. The tapered portion 813 may have slits 815 therein which allow the tapered portion to be compressed tightly to the rod 801 once it is positioned in the open-back member 820. The sleeve 812 also includes a nut threaded to portion 813 with a flange 819 on the nut 811. The spacing "LC" may be utilized to act as a gauge to assure that the nut 811 is spaced properly on the locking sleeve 812. If the nut 811 is threaded too far away from the tapered portion 813, it won't fit in cavity 513. This is advantageous because if the nut 811 is too far away it could disassemble from the threaded portion 814 which would not be desirable. If the nut 811 is threaded too closely toward the tapered portion 813, it could interfere with the clearance required for insertion of the slideable member through the opening 821 in the open-back member 820 into the corresponding cavity 822 which has a tapered surface to mate with the tapered portion 813 of the sleeve 812. Thus, the length "LC" of the cavity 513 provides a gauge which assists in properly spacing the nut 811 on the sleeve 812 to provide the length "LS" as shown in FIG. 6 before maneuvering the slideable member with instrument 501 along the rod 801 to locate it in open-back member 820.

The use of the instrument 501 will be described in conjunction with the slideable member 810 as shown in FIGS. 6–11, although it is understood that this instrument could be utilized with other types of slideable members along a corresponding rod or base member.

The slideable member 810 is adapted for being inserted through opening 821 in open-back member 822. The member 822 has a desired or predetermined location along rod 801. Member 822 may be already secured in its desired location or it may be being held (manually or otherwise) in its desired location. The specific location or means of holding such location is not shown herein. The object is to slide the slideable member to the open-back member to then locate the slideable member therein. FIG. 6 shows the slideable member 810 located on the rod 801 spaced away longitudinally from the open-back member 820. The rod 801 is positioned above the opening 821 of member 822. The instrument 501 is applied to the slideable member 810 as shown in FIG. 7 to straddle member 810 in the cavity 513 between extending members 510 and 511 of instrument 501. A longitudinal force (in the direction of the arrow of FIG. 7) is then applied to the instrument 501 to slide the slideable member 810 in the desired longitudinal direction along the rod 801 to the desired location above the opening 821 of the open-back member 820 as shown in FIG. 8. A downward force is then applied to the instrument (in the direction of the arrow of FIG. 8) to cause the slideable member to pass through the opening 821 of the open-back member 820 for locating therein in the corresponding tapered cavity 822 as shown in FIG. 9. A longitudinal force is then applied to the instrument (in the direction of the arrow of FIG. 9) to cause the tapered portion 813 on the slideable member 810 to slide further into and tighten against the corresponding tapered cavity 822 of the open-back member 820, to the position shown in FIG. 10, thus securely seating the slideable member in place. This also causes the slits 815 in the tapered portion 813 of sleeve 812 to compress inwardly to tighten the slideable member 810 on the smooth rod 801. As shown in FIG. 11, the nut 811 is threaded up to the open-back member 820 to more securely locate the slideable member 810 and open-back member 820 in the desired position on the rod 801.

It is noted that any suitable materials may be utilized for instrument 501. One such material is stainless steel. The slideable member, rod, and open-back member in the spinal related embodiment disclosed in FIGS. 6-11 are implantable devices, and as such as made of any suitable implantable material. One such material is 22-13-5 stainless steel. Regarding manufacturing methods, any suitable methods may be utilized.

While this invention has been described and exemplified in terms of a particularly advantageous embodiment, those skilled in the art can appreciate that modifications can be made without departing from the spirit and scope of this invention.

I claim:

1. A surgical instrument for maneuvering a slideable member along an elongated rod, the instrument including a distal tip and a single-membered, nonpivotal elongated handle extending therefrom, the tip including first and second extending members spaced apart from each other and rigidly connected by an interconnecting portion therebetween, thus providing a cavity having fixed, nonadjustable spacing between the first and second extending members for receiving the slideable member, and wherein the first and second extending members each have a side which includes a recess extending into the extending member.

2. The instrument of claim 1 wherein the handle connects to the distal tip more toward the second extending member than the first extending member.

3. A surgical instrument for maneuvering a slideable member along an elongated rod, the instrument including a distal tip and a single-membered, nonpivotal elongated handle extending therefrom, the tip including first and second extending members spaced apart from each other and rigidly connected by an interconnecting portion therebetween, thus providing a cavity having fixed, nonadjustable spacing between the first and second extending members for receiving the slideable member, and wherein the interconnecting portion and the first and second extending members are each substantially planar and wherein the extending members are each substantially perpendicular to the interconnecting portion.

4. The instrument of claim 3 wherein the elongated handle forms an angle of about 120° with the interconnecting portion.

5. A surgical instrument for maneuvering a slideable member along an elongated rod, the instrument including a distal tip and an elongated handle extending therefrom, the tip including first and second extending members spaced apart from each other and connected by an interconnecting portion therebetween, thus providing a cavity between the first and second extending members for receiving the slideable member, and wherein the first and second extending members each have a side which includes a recess extending into the extending member, and wherein the first and second extending members each have a top side which connects to the interconnecting member and wherein the recessed sides of the respective extending members are located adjacent to the respective top sides.

6. A method of utilizing a surgical instrument in conjunction with a slideable member located along an elongated rod and wherein the instrument includes a distal tip and an elongated handle extending therefrom, the tip including first and second extending members spaced apart from each other and rigidly connected by an interconnecting portion therebetween, thus providing a cavity having fixed spacing between the first and second extending members, the cavity being open on at least one side and being adapted for accepting a portion of the slideable member therein for straddling the slideable member between the first and second extending members, the method including the following steps:
 (a) straddling the slideable member in the cavity between the first and second extending members of the instrument; and
 (b) applying longitudinal force to the instrument to slide both the whole instrument and the straddled slideable member longitudinally along the rod to the desired location along the rod.

7. A method of utilizing a surgical instrument in conjunction with a slideable member located along an elongated rod wherein the slideable member is adapted for being inserted through an opening in an open-back member, and wherein the instrument includes a distal tip and an elongated handle extending therefrom, the tip including first and second extending members spaced apart from each other and rigidly connected by an interconnecting portion therebetween, thus providing a cavity having fixed spacing between the first and second extending members, the cavity being open on at least one side and being adapted for accepting a portion of the slideable member therein for straddling the slideable member between the first and second extending members, the method including the following steps:
 (a) positioning the elongated rod over the opening to the open-back member;
 (b) straddling the slideable member in the cavity between the first and second extending members of the instrument;
 (c) applying longitudinal force to the instrument to slide both the whole instrument and the straddled slideable member in the desired longitudinal direction along the rod to the desired location above the opening of the open-back member; and
 (d) pushing down on the instrument to cause the slideable member to pass through the opening of the open-back member for locating therein.

8. The method of claim 7 wherein the slideable member includes a tapered portion for mating location within a corresponding tapered cavity in the open-back member, the method further including, applying longitudinal force to the instrument and thus to the slideable member once it is located in the open-back member to cause the taper on the slideable member to slide further into and tighten against the taper on the open-back member, and thus securely seating the slideable member in place.

9. The method of claim 8 wherein the slideable member includes a threaded portion with a threadedly engaged nut, the method further including the step of threading the nut up to the open-back member to more securely locate the slideable member and open-back member in the desired position on the rod.

10. A method of utilizing a surgical instrument in conjunction with a slideable member located along an elongated rod and wherein the instrument includes a distal tip and an elongated handle extending therefrom, the tip including first and second extending members spaced apart from each other and connected by an interconnecting portion therebetween, thus providing a cavity having a length between the first and second extending members, the cavity being open on at least one side and being adapted for accepting a portion of the slideable member therein for straddling the slideable member between the first and second extending members, the method including the following steps:

(a) aligning the length of the cavity so that it is substantially parallel with the elongated rod;
(b) straddling the slideable member in the cavity between the first and second extending members of the instrument; and
(c) applying longitudinal force to the instrument to slide both the whole instrument and the straddled slideable member longitudinally along the rod to the desired location along the rod.

* * * * *